(12) United States Patent
Chadda et al.

(10) Patent No.: US 7,880,027 B2
(45) Date of Patent: Feb. 1, 2011

(54) METHOD FOR PRODUCING UNSATURATED CARBOXYLIC ACIDS AND NITRILES

(75) Inventors: Nitin Chadda, Radnor, PA (US); Scott Han, Lawrenceville, NJ (US); Andrew Michael Lemonds, Schwenksville, PA (US)

(73) Assignee: Rohm and Haas Company, Philadelphia, PA (US)

(*) Notice: Subject to any disclaimer, the term of this patent is extended or adjusted under 35 U.S.C. 154(b) by 407 days.

(21) Appl. No.: 12/229,118

(22) Filed: Aug. 20, 2008

(65) Prior Publication Data
US 2009/0054678 A1 Feb. 26, 2009

Related U.S. Application Data

(60) Provisional application No. 60/965,858, filed on Aug. 23, 2007.

(51) Int. Cl.
C07C 253/24 (2006.01)
C07C 51/21 (2006.01)

(52) U.S. Cl. ........................ 558/319; 562/549

(58) Field of Classification Search ........................ None
See application file for complete search history.

(56) References Cited

U.S. PATENT DOCUMENTS

| 5,141,732 A | 8/1992 | Haardt et al. |
| 5,271,835 A | 12/1993 | Gorawara et al. |
| 6,258,992 B1 | 7/2001 | Karim et al. |
| 6,544,409 B2 | 4/2003 | De Souza |
| 6,607,795 B1 | 8/2003 | Yang et al. |
| 6,664,416 B2 | 12/2003 | Tanimoto et al. |
| 6,736,963 B2 | 5/2004 | Pradhan et al. |
| 7,009,075 B2 | 3/2006 | Hazin |
| 2003/0094400 A1 | 5/2003 | Levy et al. |
| 2004/0154959 A1 | 8/2004 | Schroebrechts et al. |
| 2006/0004228 A1 | 1/2006 | Hazin |
| 2006/0069279 A1 | 3/2006 | Mamedov et al. |

FOREIGN PATENT DOCUMENTS

| CA | 2453155 A1 | 6/2004 |
| JP | 2001342169 A | 12/2001 |
| WO | WO 03/068893 | 8/2003 |

OTHER PUBLICATIONS

Ushikubo, T., Database WPI Week 200230, Thomas Scientific, London, GB; AN 2000-247254, XP002505943 & JP 2001342169A Mitsubishi Chem Corp, Dec. 11, 2001 abstract.

*Primary Examiner*—Kamal A Saeed
(74) *Attorney, Agent, or Firm*—Tifani M. Cottingham

(57) ABSTRACT

The present invention relates to an improved alkane (amm) oxidation process in which sulfur-bearing impurities present in the alkane feedstock are removed upstream from the (amm) oxidation reaction.

10 Claims, No Drawings

METHOD FOR PRODUCING UNSATURATED CARBOXYLIC ACIDS AND NITRILES

This application claims the benefit of priority under 35 U.S.C. §119(e) of U.S. Provisional Application No. 60/965,858 filed Aug. 23, 2007.

The present invention relates to a method for alkane (amm)oxidation to unsaturated carboxylic acids or nitriles using a mixed metal oxide (MMO) catalyst. Specifically, it relates to a method for removing sulfur impurities in the feed and a method for the selective removal of reduced forms of sulfur impurities. More specifically, it relates to the removal of sulfur impurities from propane or a propane oxidation feed that is oxidized to acrylic acid.

As used herein, the use of the term "(meth)acrylate" refers to both acrylates and methacrylates. Similarly, the term "(meth)acrylic" refers to either acrylic or methacrylic; the term "(meth)acrylic acid" refers to either acrylic acid or methacrylic acid.

As used herein the term (amm)oxidizing is meant to refer to both the processes in which mixtures of propane, ammonia, and oxygen are converted in the presence of a catalyst to a nitrile as the primary product and in which mixtures of propane, and oxygen are converted in the presence of a catalyst to a carboxylic acid as a product.

Acrylic acid (AA), one example of an unsaturated carboxylic acid, and acrylonitrile, one example of a nitrile are used in a wide variety of applications. Typical end-use applications include: acrylic plastic sheeting; molding resins; polyvinyl chloride modifiers; processing aids; acrylic lacquers; paints and coatings; building products; floor polishes; sealants; auto transmission fluids; crankcase oil modifiers; automotive coatings; ion exchange resins; cement modifiers; water treatment polymers; electronic adhesives; metal coatings; and acrylic fibers. AA is especially prized in these applications and others because of the hardness it imparts to the products in which it is used. It also enhances chemical stability and light stability, as well as ultraviolet radiation resistance, when used in certain products. Therefore, AA is often used in applications requiring resins of excellent transparency, strength, and outdoor durability. The AA market is extremely cost-sensitive; thus, any improvement in process yield, however slight, can result in significant cost-savings.

Commercial grades of propane, which may be employed as a feedstock for the production of unsaturated carboxylic acids and nitriles, typically contain a number of sulfur-bearing compounds including, but not limited to, mercaptans (RSH, namely methyl and ethyl), sulfur dioxide ($SO_2$), carbonyl sulfide (COS), hydrogen sulfide ($H_2S$), sulfides (RSR), and disulfides (RSSR), where R is an alkyl or aryl group. Typical specification levels for commercial grade range from 100 to 150 ppm by weight of total elemental sulfur.

The adsorption and reaction of these sulfur compounds on the mixed metal oxide catalysts useful for alkane (amm)oxidation can be deleterious to catalyst performance and stability. Of particular concern is a loss of long-term performance, especially long-term catalyst stability. The adsorption onto and subsequent, reaction of reducing forms of sulfur compounds, such as hydrogen sulfide, with an MMO alkane oxidation catalyst may reduce the oxidation state of the catalyst's constituent catalytic metals. Thus, the redox properties, which are crucial to the catalytic properties of these MMOs, may be affected, and the presence of these reducing compounds in the alkane oxidation feed may therefore deteriorate the catalyst's performance and/or stability, resulting in a state known in the art as "sulfur poisoning." Low levels of oxidizing forms of sulfur in the (amm)oxidation feed are not deleterious to MMO catalysts and can in fact improve catalyst lifetime and enhance the (amm)oxidation yield. The MMO catalyst performance is also improved when the catalyst is prepared to contain sulfur oxides as promoters. Thus, a need exists for the selective removal of the reducing forms of sulfur from the alkane (amm)oxidation feeds.

Japanese published patent application 2001-342169 discloses a method of producing acrylic acid and/or acrylonitrile containing lower amounts of sulfur impurities by an adsorption process. The reaction is conducted using a catalyst containing Mo, V, and Te or Sb as required elements, from propane wherein the total feed gas contains less than 200 ppm sulfur. The application discloses the use of zinc oxide, activated carbon, copper oxide, iron oxide, ruthenium, nickel, palladium, or aluminum desulfurizing adsorbents for eliminating oxidizing and reducing forms of sulfur compounds such as $H_2S$, COS, carbon disulfide, $SO_2$, RSH, RSR, RSSR, and thiophene.

For the commercial production of acrylic acid or acrylonitrile by propane (amm)oxidation, the use of the desulfurizing adsorbents disclosed in JP 2001-342169 presents a problem in that these materials are consumed over time as they accumulate or react with the sulfur impurities. They must therefore be periodically regenerated or replaced, hence the sulfur removal itself is conducted in a batch or semi-continuous operation. Regeneration or replacement of the adsorbent becomes cumbersome and expensive for large scale continuous processes. Thus, the need for processes for producing (meth)acrylic acid or (meth)acrylonitriles from alkanes by processes, in, which sulfur is removed continuously are needed.

Additionally, in order for methods of producing (meth)acrylic acid or (meth)acrylonitrile from alkanes to benefit from oxidized forms of sulfur present in the alkane oxidation feed, methods in which reduced forms of sulfur are selectively removed are needed.

The improved alkane (amm)oxidation process of the present invention avoids the problem of sulfur poisoning and increases process efficiency by providing for the integration of continuous sulfur removal techniques with the alkane (amm)oxidation technology known in the present art and provides a method for the selective removal of sulfur from alkane (amm)oxidation reactions.

Effective sulfur removal techniques of the present invention largely comprise, but are not limited to, adsorption and absorption unit operations. For the former, the commercial grade alkane feedstock is passed over a solid adsorbent which is held in a bed or suspended in a liquid, onto which the sulfur selectively adsorbs. The adsorbent must be periodically regenerated or replaced; hence, the sulfur removal is conducted in a batch or semi-continuous mode. Absorption techniques subject the feedstock to a liquid absorbent; the sulfur impurity is retained by chemical reaction or solvation with the absorbent. Absorption may be operated in continuous or batch modes.

In one aspect of the present invention, there is provided, a process for (amm)oxidizing alkanes to unsaturated carboxylic acids or nitriles comprising:
  i. reacting an alkane with oxygen, oxygen and ammonia, or an oxygen and ammonia containing gas in the presence of an oxidation catalyst to yield a product comprising at least one unsaturated carboxylic acid or nitrile and a concentration of saturated carboxylic acid or nitrile comprising a sulfur impurity concentration; and
  ii. lowering the sulfur impurity concentration by an absorption process.

In a second aspect of the present invention there is provided a process for (amm)oxidizing alkanes to unsaturated carboxylic acids or nitriles comprising:

i. reacting an alkane with oxygen, oxygen and ammonia, or an oxygen and ammonia containing gas, such as air, in the presence of a catalyst to yield a product comprising at least one unsaturated carboxylic acid or nitrile and a concentration of saturated carboxylic acid or nitrile comprising a sulfur impurity concentration; wherein the sulfur impurity concentration comprises reduced forms of sulfur.

ii. removing selectively the reduced sulfur form impurity concentration by an adsorption process from an alkane or (amm)oxidation feed.

The method comprises reacting in a single reaction vessel at least one $C_3$-$C_8$ straight chain or branched alkane. As used herein, the term "$C_3$-$C_8$ straight chain or branched alkane" means a straight chain or branched chain alkane, although longer alkanes may also be used, having from 3 to 8 carbons atoms per alkane molecule, for example, propane, butane and pentane. Particularly, $C_3$-$C_5$ straight chain or branched alkanes are examples of alkanes of the present invention.

When the alkane comprises propane, the unsaturated carboxylic acid comprises acrylic acid, and the nitrile comprises acrylonitrile. The alkane is reacted with oxygen or oxygen present in a mixture with an inert gas, such as nitrogen, in the presence of a catalyst at a temperature ranging from upper limits of 550° C., 480° C., and 400° C. to lower limits of 250° C., 275° C., and 300° C. All temperature ranges are inclusive and combinable.

In one embodiment, the catalyst comprises a mixed metal oxide (MMO) having the empirical formula

$A_aM_bN_cX_dZ_eO_f$ wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and wherein, when a=1, b=0.01 to 1.0, c=0.01 to 1.0, d=0.01 to 1.0, e=0 to 0.1, and f is dependent on the oxidation state of the other elements.

The reactants are admixed or otherwise provided with a diluent. The diluent is preferably a gas at room temperature and ambient pressure; and is inert to the reaction environment under the existing reaction conditions. Suitable gases include nitrogen, argon, helium and the like. The amount of diluent is not particularly important, however, it is preferably present in an amount of from greater than 0.1 mole percent to less than 70 mole percent, based on the total feed to the reactor, when used. Also, steam may be present in the feed gas in an amount varying from zero to 50 percent.

Suitable reaction vessels are designed to conduct vapor-phase, heterogeneous reactions and include but are not limited to fixed bed, fluidized bed, plate and frame, and microchannel reactors. Where propane is used as the starting alkane and air is used as the oxygen source, the reaction vessel may be a fixed bed system or a fluidized bed system. The proportion of air to be supplied to the reaction system is important for the selectivity for the resulting acrylic acid or nitrile. For acrylic acid, the proportion of air supplied is usually at most 25 moles, but usually ranges from 0.2 to 18 moles per mole of propane, whereby high selectivity for acrylic acid can be obtained. This reaction can be conducted under atmospheric pressure. However, the reaction may also be conducted under a slightly elevated pressure or slightly reduced pressure. With respect to other alkanes, for example isobutane, the composition of the feed gas may be selected in accordance with the conditions for propane.

Typical reaction conditions for the oxidation of propane to acrylic acid or methacrylic acid or acrylonitrile may be utilized in the practice of the present invention. The process may be practiced in a single pass mode where only fresh feed is fed to the reactor, or in a recycle mode where at least a portion of the reactor seffluent is returned to the reactor. General conditions for the process of the present invention are as follows: the reaction temperature ranges from upper limits of 550° C., 480° C., 400° C. to lower limits of 250° C., 275° C. and 300° C.: to the gas space velocity, "SV", in the vapor phase reactor is typically within a range from upper limits of 10,000, 6,000, and 2,000 hr–1 to lower limits of 300, 200, and 100 hr–1; the average contact time with the catalyst can range from upper limits of 10, 8, 6, and 2 seconds to lower limits of 0.01, 0.01, 0.5, and 1 seconds; and the pressure in the reaction zone usually ranges from 0 to 75 psig, but is typically no more than 50 psig. All of the aforementioned range values are inclusive and combinable within a given set. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

As a result of reacting at least one alkane with oxygen, oxygen and ammonia, or an oxygen and ammonia containing gas, such as air, in the presence of at least one catalyst, a product is formed that comprises a least one unsaturated carboxylic acid or nitrile and a concentration of a saturated carboxylic acid or nitrile containing at least one sulfur impurity. As used herein by "sulfur impurity" is meant $H_2S$, COS, carbon disulfide, $SO_2$, RSH, RSR, RSSR, and thiophene.

In one embodiment, these sulfur compounds are removed by physical absorption. The sulfur compounds are removed by contacting the alkane or (amm)oxidation feed gas with an absorbent in an absorption zone. As used herein "absorption zone" is defined as the physical place in the reaction process where the sulfur compounds are absorbed into the absorbent. The absorbent containing the sulfur compound is then cycled continuously to a desorption zone, similarly, where the absorbed sulfur compounds are removed, for example, by flash evaporation or stripping. The absorbent is continuously collected from the desorption zone and returned to the absorption zone; the sulfur compounds collected in the desorption zone can then be subjected to disposal. Suitable physical absorbents for sulfur compounds include, but are not limited to, methanol, dimethylethers of polyethylene glycols, propylene carbonate, sulfolane, and 1-acetylmorpholine. A non limiting example of a typical physical absorption process is pressure swing absorption.

In another embodiment, sulfur compounds are removed by chemical absorption, which operates similar to the physical absorption process in that the sulfur compounds are absorbed in an absorption zone and desorbed in a desorption zone. The key difference is that the sulfur compounds chemically interact with the absorbent by reversible chemical reactions or complexation. Suitable chemical absorbents for sulfur compounds include aqueous organic amines, for example, monoethanolamine, diethanolamine, diglycolamine, and methyldiethanolamine and aqueous alkali carbonates, for example, potassium carbonate. An example of a commercial chemical absorption process is Petrolite's Sulfa-scrub HSW process in which sulfur is removed from natural gas by absorption into aqueous triazines.

In another aspect of the invention, the process is characterized as the selective removal of reduced sulfur forms of sulfur compounds from the alkane or (amm)oxidation feed gas. Examples of such reduced forms of sulfur include but are not limited to $H_2S$, RSH, RSR, RSSR, and thiophene. Selective adsorbents may be used for batch or semi-continuous sulfur compound removal, and selective absorbents may be used for continuous sulfur compound removal. An example of one useful adsorbent is iron oxide. Sulfur compounds react with the iron oxide, which is consumed and must eventually be regenerated or disposed. Hydrogen sulfide, for example, reacts to form iron sulfide and water. Mercaptans react to form ferric mercaptides. The spent adsorbent is regenerated by reaction with oxygen. Iron sulfide, for example, is reacted with oxygen to recover iron oxide and elemental sulfur. The iron oxide is typically provided in a fixed bed. An implement commonly referred to as an "iron sponge" comprises impregnating wood chips or shavings with iron oxide particles.

Similarly, sulfur may also be adsorbed onto zinc oxide particles, which are typically provided as a slurry. The zinc oxide particles are typically suspended in an aqueous zinc acetate solution. The adsorption mechanism is similar to adsorption onto iron oxide, however unlike iron sulfide, zinc sulfide cannot be regenerated.

Alternatively, sulfur can be adsorbed onto molecular sieves. Sulfur components are removed by the action of physical adsorption, not chemical reaction. Regeneration is achieved by passing hot gas over the adsorbent at pressures of atmospheric pressure and below.

Lastly, sulfur removal may be accomplished via commercial adsorption technologies. One non-limiting example such a commercial technology is the SulfaTreat 114 process using the Engelhard Selexsorb adsorbent.

What is claimed is:

1. A process for alkane ammoxidation to unsaturated carboxylic acids or nitriles comprising:
   i. reacting an alkane with oxygen, oxygen and ammonia, or an oxygen and ammonia containing gas in the presence of an oxidation catalyst to yield a product comprising at least one unsaturated carboxylic acid or nitrile and a concentration of saturated carboxylic acid or nitrile comprising a sulfur impurity concentration; and
   ii. lowering the sulfur impurity concentration by an absorption process.

2. The process of claim 1 wherein the absorption process is physical absorption.

3. The process of claim 1 wherein the absorption process is chemical absorption.

4. The process of claim 1 wherein the absorption process is continuous.

5. The process of claim 1 in which the alkane is propane, and the unsaturated carboxylic acid is acrylic acid.

6. The process of claim 1 in which the oxidation catalyst is a mixed metal oxide having the empirical formula

wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and wherein, when a=1, b=0.01 to 1.0, c=0.01 to 1.0, d=0.01 to 1.0, e=0 to 0.1, and f is dependent on the oxidation state of the other elements.

7. The process of claim 1 in which the sulfur impurities are continuously removed by absorption.

8. A process for (amm)oxidizing alkanes to unsaturated carboxylic acids or nitrites comprising:
   i. reacting an alkane with oxygen, oxygen and ammonia, or an oxygen and ammonia containing gas, such as air, in the presence of a catalyst to yield a product comprising at least one unsaturated carboxylic acid or nitrile and a concentration of saturated carboxylic acid or nitrile comprising a sulfur impurity concentration; wherein the sulfur impurity concentration comprises reduced forms of sulfur; and
   ii removing selectively the reduced sulfur form impurity concentration by an aborption process from an alkane or (amm)oxidation feed.

9. The process of claim 8 wherein the absorption process is physical absorption.

10. The process of claim 8 wherein the absorption process is chemical absorption.

* * * * *